(12) United States Patent
Thramann

(10) Patent No.: US 9,149,319 B2
(45) Date of Patent: Oct. 6, 2015

(54) METHODS AND COMPOSITIONS FOR STABILIZATION OF A VERTEBRA

(75) Inventor: Jeffrey John Thramann, Niwot, CO (US)

(73) Assignee: LANX, LLC, Broomfield, CO (US)

(*) Notice: Subject to any disclaimer, the term of this patent is extended or adjusted under 35 U.S.C. 154(b) by 535 days.

(21) Appl. No.: 12/565,648

(22) Filed: Sep. 23, 2009

(65) Prior Publication Data

US 2010/0082073 A1   Apr. 1, 2010

Related U.S. Application Data

(60) Provisional application No. 61/099,462, filed on Sep. 23, 2008.

(51) Int. Cl.
  *A61F 2/46* (2006.01)
  *A61B 17/88* (2006.01)
  *A61B 17/70* (2006.01)
  *A61B 17/56* (2006.01)

(52) U.S. Cl.
  CPC ......... *A61B 17/8866* (2013.01); *A61B 17/8805* (2013.01); *A61B 17/7077* (2013.01); *A61B 2017/564* (2013.01)

(58) Field of Classification Search
  CPC ........... A61B 17/8866; A61B 17/8805; A61B 2017/564; A61B 17/7077
  USPC ............ 606/57, 86 A, 92–94, 279, 86 B, 105, 606/246, 248; 623/17.11–17.12
  See application file for complete search history.

(56) References Cited

U.S. PATENT DOCUMENTS

| 6,663,637 | B2 | 12/2003 | Dixon et al. |
| 6,893,466 | B2* | 5/2005 | Trieu .................. 623/17.16 |
| 7,157,428 | B2 | 1/2007 | Kusanagi et al. |
| 2003/0045938 | A1 | 3/2003 | Kohrs et al. |
| 2003/0219423 | A1 | 11/2003 | Gazit et al. |
| 2004/0243242 | A1 | 12/2004 | Sybert et al. |
| 2005/0175657 | A1 | 8/2005 | Hunter et al. |

(Continued)

FOREIGN PATENT DOCUMENTS

| EP | 0 530 804 | 3/1993 |
| EP | 1 400 252 | 3/2004 |

(Continued)

OTHER PUBLICATIONS

Ailhaud et al. (1983) "Hormonal Requirements for Growth and Differentiation of OB17 Preadipocyte Cells In Vitro", Diabete & Metabolisme (Paris) 9:125-133.

(Continued)

*Primary Examiner* — Christopher Beccia
*Assistant Examiner* — Diana S Jones
(74) *Attorney, Agent, or Firm* — Schwegman Lundberg & Woessner, P.A.

(57) ABSTRACT

Compositions and methods are provided for stabilization and treatment of vertebrae, and in particular for stabilization and treatment of a vertebra having a fracture. Compositions are provided that stabilize and heal a fracture while facilitating healing and reducing the chance for re-injury to the vertebra or adjacent vertebra. Methods include elevation of the vertebra to facilitate healing under reduced pressure situations and include leverage points to elevate the fracture before or during composition insertion.

19 Claims, 13 Drawing Sheets

(56) References Cited

U.S. PATENT DOCUMENTS

| | | | |
|---|---|---|---|
| 2005/0187560 | A1 | 8/2005 | Dietzel et al. |
| 2006/0025340 | A1 | 2/2006 | Knopf et al. |
| 2006/0036246 | A1* | 2/2006 | Carl et al. ............. 606/61 |
| 2006/0084983 | A1 | 4/2006 | Kim |
| 2006/0099182 | A1 | 5/2006 | Baltzer et al. |
| 2006/0106364 | A1 | 5/2006 | Whitlock et al. |
| 2006/0184192 | A1* | 8/2006 | Markworth et al. ......... 606/198 |
| 2007/0093825 | A1 | 4/2007 | Ferree et al. |
| 2007/0093846 | A1* | 4/2007 | Frigg et al. ............. 606/90 |
| 2007/0123986 | A1* | 5/2007 | Schaller ............. 623/17.11 |
| 2007/0213824 | A1* | 9/2007 | Trieu ............. 623/17.11 |
| 2007/0254042 | A1 | 11/2007 | Drapeau et al. |
| 2008/0019970 | A1 | 1/2008 | Gorman |
| 2009/0005821 | A1* | 1/2009 | Chirico et al. ............. 606/319 |
| 2009/0047360 | A1 | 2/2009 | Murray et al. |
| 2009/0076515 | A1* | 3/2009 | Lamartina et al. ............. 606/90 |
| 2010/0150881 | A1 | 6/2010 | Thramann |
| 2010/0233137 | A1 | 9/2010 | Thramann |
| 2011/0130836 | A1 | 6/2011 | Thramann |

FOREIGN PATENT DOCUMENTS

| | | |
|---|---|---|
| WO | WO 96 39170 | 12/1996 |
| WO | WO 03 094617 | 11/2003 |
| WO | WO 2004 032943 | 4/2004 |
| WO | WO 2005 077403 | 8/2005 |
| WO | WO 2008 089164 | 7/2008 |
| WO | WO 2008 106478 | 9/2008 |
| WO | WO 2008 151119 | 12/2008 |
| WO | WO 2009 105606 | 8/2009 |

OTHER PUBLICATIONS

Bennett et al. (1991) "Adipocytic Cells Cultured from Marrow have Osteogenic Potential", Journal of Cell Science, 99:131-139.

Kawano et al. (2003) "Mechanical Effects of the Intraarticular Administration of High Molecular Weight Hyaluronic Acid Plus Phospholipid on Synovial Joint Lubrication and Prevention of Articular Cartilage Degeneration in Experimental Osteoarthritis", Arthritis and Rheumatism, 48(7):1923-1929.

Lam and Moy (1992) "The Potential for Fat Transplantation", J. Detmatol. Surg. Oncol., 18:432-434.

Lecoeur and Ouhayoun (1997) "In Vitro Induction of Osteogenic Differentiation from Non-Osteogenic Mesenchymal Cells", Biomaterials 18:989-993.

Marko et al. (1995) "Isolation of a Preadipocyte Cell Line from Rat Bone Marrow and Differentiation to Adipocytes", Endocrinology, 136(10):4582-4588.

Novakofski (1987) "Primary Cell Culture of Adipose Tissue", Biology of the Adipocyte: Research Approaches, Van Nostrand Reinhold Company, pp. 160-197.

Pettersson et al. (1985) "Adipocyte Precursor Cells in Obese and Nonobese Humans", Metabolism, 34(9):808-812.

Smit et al. (2006) "Application of Polylactides in Spinal Cages: Studies in a Goat Model", Journal of Materials Science: Materials in Medicine, 17(12):1237-1244.

Soda and Tavassoli (1983) "Adipocyte Stem Cell: A Brief Review", International Journal of Cell Cloning, 1:79-84.

Tavassoli (1982) "In Vitro Development of Adipose Tissue Following Implantation of Lipid-Depleted Cultured Adipocyte", Experimental Cell Research, 137:55-62.

Vassaux et al. (1994) "Proliferation and Differentiation of Rat Adipose Precursor Cells in Chemically Defined Medium: Differential Action of Anti-Adipogenic Agents", Journal of Cellular Physiology, 161:249-256.

Williams et al. (1992) "Formation of a Multilayer Cellular Lining on a Polyurethane Vascular Graft Following Endothelial Cell Sodding", Journal of Biomedical Materials Research, 26:103-117.

Williams et al. (1994) "Liposuction-Derived Human Fat Used for Vascular Graft Sodding Contains Endothelial Cells and Not Mesothelial Cells as the Major Cell Type", Journal of Vascular Surgery, 19(5):916-923.

Yeung et al. (2006) "Short-Term Therapeutic Outcome of Intra-Articular High Molecular Weight Hyaluronic Acid Injection for Nonreducing Disc Displacement of the Temporomandibular Joint", Oral Radiology Andendodontics, 102(4):453-461.

An et al. (2006) "Intradiscal Administration of Osteogenic Protein-1 Increases Intervertebral Disc Height and Proteoglycan Content in the Nucleus Pulposus in Normal Adolescent Rabbits" SPINE, 30(1):25-32.

Duggirala et al. (1996) "Interaction of Recombinant Human Bone Morphogenetic Protein-2 with Poly(d, l Lactide-co-glycolide) Microspheres" Pharmaceutical Dev. & Tech., 1(1):11-19.

Hashiya et al. (2004) "In Vivo Evidence of Angiogenesis Induced by Transcription Factor Ets-1 : Ets-1 is Located Upstream of Angiogenesis Cascade", Circulation 109:3035-3041.

Jelic et al. (2001) "Regeneration of Articular Cartilage Chondral Defects by Osteogenic Protein-1 (Bone Morphogenetic Protein-7) in Sheep" Growth Factors, 19(2):101-113 Abstract Only.

Kang et al. (Published online Oct. 31, 2007) "Articular Cartilage Regeneration with Microfracture and Hyaluronic Acid", Biotechnology Letters, 30(3):435-439.

Liu et al (2006) "Osteochondral Defect Repair with Autologous Bone Marrow-Derived Mesenchymal Stem Cells in an Injectable, In Situ, Cross-Linked Synthetic Extracellular Matrix" Tissue Engineering, 12(12):3405-3416.

* cited by examiner

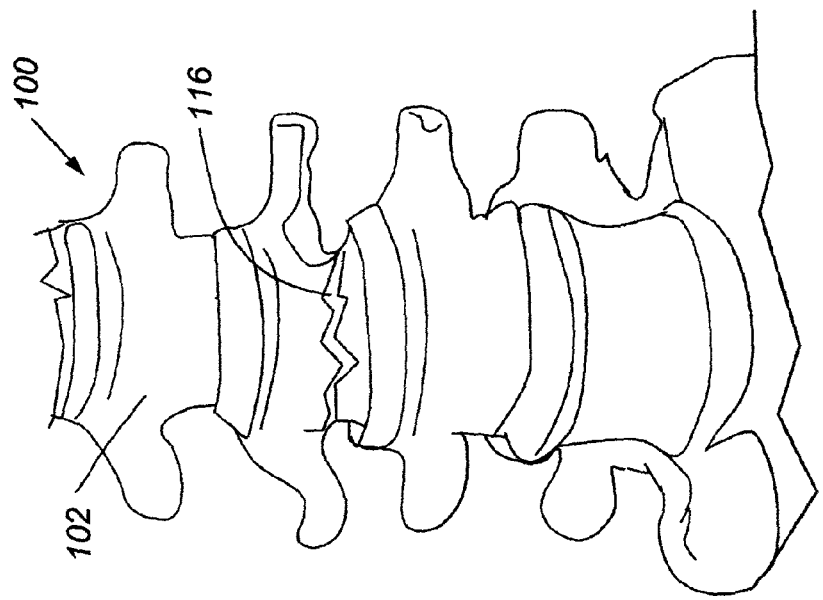
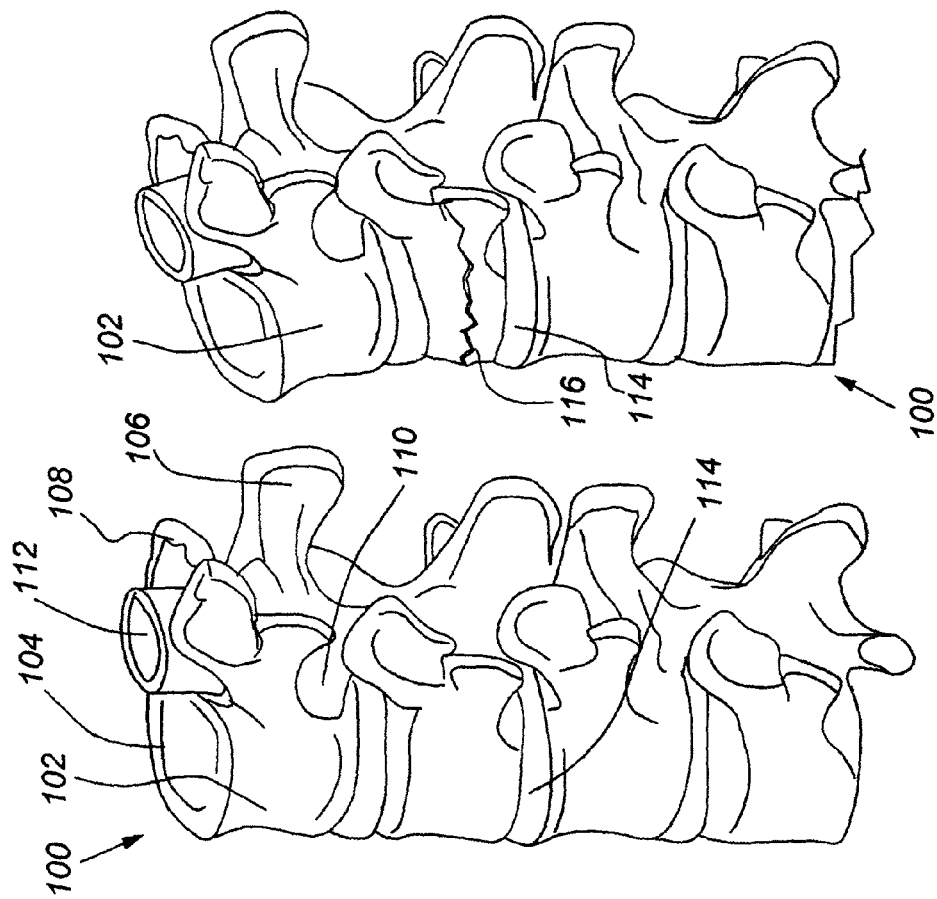
Fig. 1A  Fig. 1B  Fig. 1C

METHODS AND COMPOSITIONS FOR STABILIZATION OF A VERTEBRA

RELATED APPLICATIONS

This application claims the benefit of U.S. Provisional Application Ser. No. 61/099,462, filed Sep. 23, 2008, entitled "Compositions and Methods for Stabilization of a Vertebrae", which is incorporated herein by reference in its entirety.

TECHNICAL FIELD

The invention provides methods and compositions for stabilizing and repairing a compression fracture in a damaged vertebra, and more particularly to methods and compositions for stabilizing and repairing a fracture in a damaged vertebra where the damaged vertebra is elevated and then treated such that the pre-fracture structural parameters of the injured vertebra are maintained.

BACKGROUND

The spine consists of a series of vertebrae between each of which is a connective tissue pod termed a disc. Each vertebra is an irregularly shaped bone that consists of two parts: an anterior segment (front) and a posterior portion (neural arch). When the vertebrae and discs are in normal healthy condition they form a strong pillar for the support and shock absorption of the head and trunk, as well as forming a canal for the protection of the spinal cord.

Every vertebra also includes two transverse processes and one spinous process. These processes are posterior to the vertebrae, with the spinous process coming out of the back of the vertebrae and the transverse processes coming out the back of the vertebrae to the left and right of the spinous process.

Injury to a vertebra may occur through a wide number of avenues; one common injury is vertebral compression fracture. Vertebral compression fractures are a compression or squishing of a vertebra into a smaller height. Compression fractures are most common in patients that have suffered a traumatic accident, especially where the patient is elderly, and in patients with osteoporosis due to the vertebrae's bone loss or thinning.

Conventional treatment for a patient with a compression fracture is typically targeted at alleviating pain associated with the damaged vertebra. Pain management is typically through a combination of rest, pain medication(s), external bracing, stretching, and strengthening regimens. However, in some cases, more aggressive treatment is required when the vertebral collapse is severe or the pain unmanageable. In such cases a procedure known as "vertebroplasty" is utilized by directly injecting bone cement into the damaged vertebra to stabilize the fracture and prevent further collapse. Another procedure is "Kyphoplasty" where a balloon is placed into the fracture site and blown up to elevate the fracture. The balloon is removed and bone cement used to fill the void and hold all or some of the elevation at the fracture site.

Other techniques for treating compression fractures include wafer stacking or bag insertion into a compressed vertebra in order to elevate the bone until the vertebra is rigid, as well as other like procedures. Concerns with the above techniques include patient re-injury, where, over time, the originally injured vertebra or adjacent vertebrae undergo additional fracture. As proposed in the present disclosure, these injuries can be due to a difference in the modulus of these devices and materials from the modulus of cancellous bone, allowing for increased stress on the bone and adjacent vertebrae. This increase in bone stress can result in enhanced risk for re-injury to the vertebra or injury to a new adjacent area, i.e., the injured vertebra and adjacent vertebrae. Further, conventional therapies rely on injection and elevation of the vertebra under load conditions, i.e., the volume of the injected material is placed while the fracture site is not actively being reduced. Such methods have limited success in reproducing full elevation of the fracture, and rather have focused on stabilizing the fracture site and thereby reducing pain to the patient.

Therefore, there is a need in the art to provide alternative therapeutics for treatment of compression and other like fractures, and in particular to provide therapeutic compositions and methods that result in the placement of a stabilizing material while the fracture is being activity reduced as well as minimizing the risk of re-injury to the site or adjacent sites after treatment.

The present invention is directed toward overcoming one or more of the problems discussed above, especially in relation to techniques for addressing compression fractures in vertebrae.

SUMMARY OF THE EMBODIMENTS

The present invention provides methods and compositions for treating a compression or other like fracture in a patient in need thereof. For purposes herein a "patient" refers to a mammal, for example, a human, having one or more compression fractures in vertebrae of their spine (compression fracture generally referring to a compressing or squishing of a vertebra to a smaller height within the spine). In some embodiments, the patient is a human and has an osteoporotic compression fracture, including such fractures to the cervical, thoracic and/or lumbar vertebrae.

In some aspects, embodiments herein include methods for elevating a fracture site prior to or during injection/incorporation of materials into the injury site. Elevation embodiments herein provide significant improvement over conventional treatment methodologies in that a significant portion of stress and strain on the injured vertebrae and spinal column is removed from the damaged vertebrae during injection of fracture treating materials. The combined result of elevating the fracture and using fracture treating materials is to provide a more durable vertebra (having a more appropriate amount of material within the fracture site and a more appropriate shape within the fracture) that is less likely to re-injure and is less likely to result in injury to adjacent vertebrae.

Aspects of the present invention also provide methods for elevating a fracture site in need of the fracture treating material where the elevated site having an injured vertebra can be expanded to pre-injury dimensions in the absence of compressed or load forces. A fracture treating material, including, for example, state of the art bone cements such as REFOBACIN®, OSTEOSPONGE®, and other fracture treating materials, can be added to the fracture site during or after elevation.

In one illustrative elevation embodiment, pins or other like instruments are inserted into a vertebra to provide a way to transmit force to the vertebra on each side of a fracture such that the vertebra may be manipulated to elevate the fracture. The pins may then be moved toward or away from one another, depending on their positions relative to the fracture to elevate the fracture. For example, a pin or other like instrument is inserted into and through each of the right and left vertebral pedicle at the level of the fracture (each of these pins herein referred to as a pedicle pin). Each pedicle pin can extend into the vertebra body and into the site of injury of the vertebra. Each pedicle pin will extend away or posteriorly out of the pedicle site and from the skin of the patient by at least 2 to 3 inches, although this length is variable and dependent on each particular patient. In some embodiments the pins are positioned in the vertebral pedicles within a pedicle sleeve to ensure that the pins can be leveraged within the vertebra (see below).

In other embodiments the pins are positioned to the lateral sides of the pedicle (left and right) and are therefore referred to as extrapedicular pins.

In still other embodiments, one or more pins (or other like instrument) can be placed into a spinous process of a vertebral segment below the fracture site, typically within three segments below the fracture site, or within two segments below the injury site, or within one segment below the fracture site. This pin is referred to as a spinous pin or spinous process pin. As with the pedicle pins, the spinous process pin extends from the rear or posterior exterior surface of the spinous process and from the skin of the patient by at least 2 to 3 inches, although as above, this distance can be variable dependent on the particular needs of the patient. The spinous pin is inserted into the vertebra to a depth that ensures that the pin is secure and anchored in the bone. The pins thereby provide points at which to exert force on the posterior side of the injured vertebra (at and below the compression site) and thereby lift or elevate the compressed side of the vertebra (the elevation being adjustable, but preferably to the extent of an uninjured vertebra).

Other embodiments also include insertion of pins (right and left) above the site of injury and spinous process pin below the site of injury, in order to provide several points at which to exert a force on the posterior side of the injured vertebra, or use of anchor points below the site of injury, for example in a right and left pedicle below the site of the injury or right and left extrapedicular pins; aspects of the invention include any combination of anchor points that allow elevation of the fracture site using pins or other like instruments to provide a leverage by which the fracture site is elevated.

Aspects of the invention also provide methods by which a surgeon or other like user can compress the ends of, for example, the pedicle pins toward the spinous pin (or other leverage point), thereby providing compression that acts like a lever, where the pedicle pins act as one point against which the superior endplate of the fractured vertebra is elevated. The spinous process pin can act as a stability point for the leverage. The elevated compression fracture can then be stabilized in this position by providing a binding element for holding the compressed pins in the compressed alignment. Binding elements can include elastic bands, ties, plates, screws, wires, clamps, etc.

Aspects of the invention also provide methods by which a surgeon or other like user can move the ends of two or more pins away from each other to manipulate the fractured vertebra.

Aspects of the invention also include injection of a fracture treating material directly into an elevated compression fracture of the invention via one or more pins, where the pins are positioned at the level of the fracture. In one embodiment, one or more pins are hollow, defining a channel, and are used as conduits for injection of the material into the fracture site. Pin embodiments for this use would require an adequate channel to ensure that the fracture treating material could be fully injected into an injury site. In some instances multiple pins are hollow and fracture treating material is deposited into the compression site via multiple pins.

In further embodiments, an additional hollow needle is inserted into the elevated fracture site to deliver the fracture treating material. In such instances the pins are not used to deliver the material as the pins are located above or below the injury site and therefore do not have the capacity to deliver the fracture treating material to the fracture site.

In some embodiments, where the surgeon has concern regarding the strength of an insertion site, for example, a spinous process site, an amount of bone cement can be injected into the site to ensure durability of the site for anchor purposes. The bone cement can be injected into the site prior to or during insertion of the pin.

Other aspects include maintaining fracture sites that have been elevated and treated with appropriate amounts and types of bone fracture treating material until the inserted material has fully set in the injury site. In one embodiment, a piston is used to drive excess material through the pedicle pin or other delivery device and into the fracture site, thereby ensuring that no material is released and set outside the injured vertebra site. Once the site is treated and the material hardened, the elevation of the site is released and the pins removed. In some embodiments, after the fracture treating material has set, excess material may be removed with the delivery device. For example the sprue of material extending away from the treatment site may be broken by bending, rotating, or pulling on the sprue or delivery device or it may be cut from the mass deposited at the treatment site and removed along with or separately from the delivery device.

Aspects of the invention, therefore, provide methods for elevating the fracture site prior to or during injection of fracture treating materials. This is a significant improvement over conventional techniques which utilize the cement to fill the site after the element to elevate the fracture has been removed (Kyphoplasty) or use wafers, bags or other non-compatible materials to elevate the site. Conventional techniques often produce inconsistent results both structurally and in healing of the vertebra, and full vertebral recovery can be limited.

In some aspects, provided herein are expandable compositions for inclusion in the fracture site, the materials having a more compatible modulus to the injured bone than conventional bone cements, such as tissue adhesives, allograft cancellous bone compositions or combinations of the above. Aspects, therefore, of the present invention include compositions for treating a compression fracture having a similar or substantially similar modulus as cancellous bone, and more particularly a similar or substantially similar modulus as cancellous bone in the injured vertebrae. These materials will be generically referred to herein as modulus appropriate compositions or materials.

These and various features and advantages of the invention will be apparent from a reading of the following detailed description and a review of the appended claims.

BRIEF DESCRIPTION OF THE DRAWINGS

FIGS. 1A, B and C provide side perspective (A and B) or anterior view (C) of a vertebral column of a normal (1A) and injured vertebra (1B and C). Note the compressed height of the injured vertebra in 1B. FIG. 1C) shows an anterior perspective of the injured vertebra in 1B, again illustrating the decreased or compressed height of the injured vertebra.

DETAILED DESCRIPTION

Figure 2:
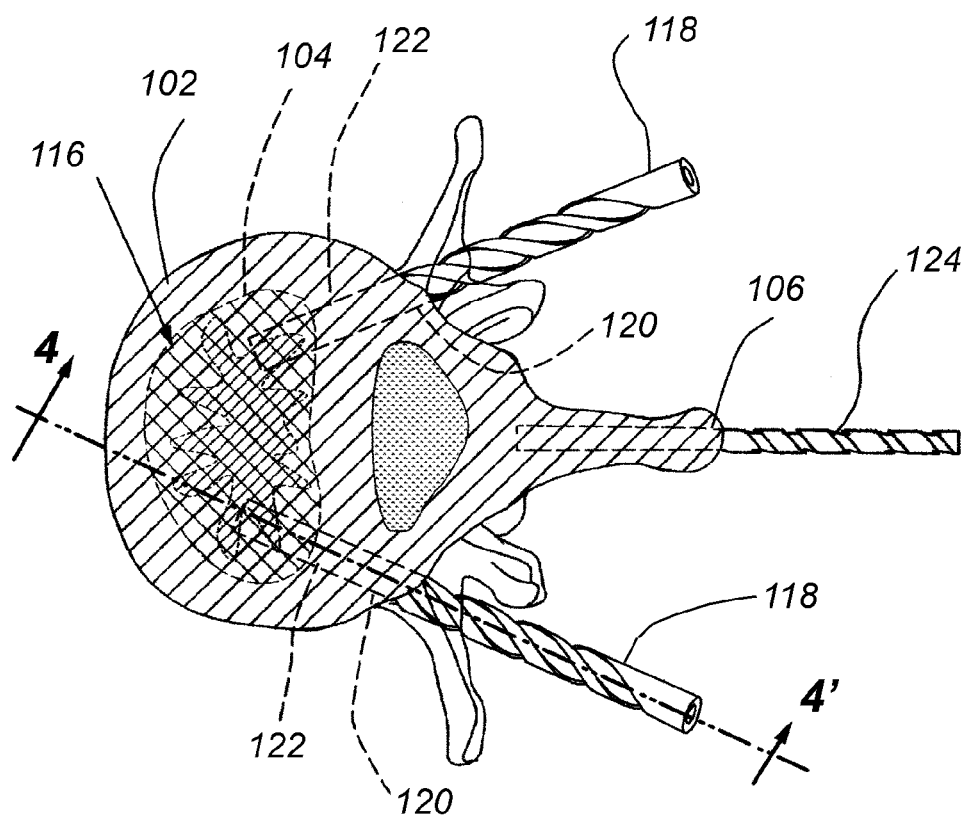
FIG. 2 is a cross-sectional view through an injured vertebra in accordance with embodiments described herein.

Surprisingly, the methods described herein provide that the use of one or more hollow manipulators inserted into bone for repositioning of a fracture, compression, or other vertebral injury are better than the use of balloons for the same purpose. Typically, balloons are inflated to elevate the collapsed portion of the vertebra and close a fracture, then deflated before injection of a fracture treating material. However, deflation of the balloon in many instances causes the fracture to reopen and allows the vertebra to collapse back toward the injured condition resulting in incomplete restoration of vertebral height. Hollow manipulators, as described herein, can, in some embodiments, both reposition the injured vertebra and hold such position until after the fracture treating material is injected and set.

Embodiments herein provide treatment strategies and methods that result in providing a more consistently and fully expanded vertebra, and further provide for a more stabilized and less prone-to-injury repair site given the improved delivery methods described herein. Embodiments include elevating a compression site of an injured vertebra prior to or during insertion of fracture treating material to thereby improve the amount and positioning of material delivered into the site and to relieve pressure on the site during injection and setting of the material.

Elevation of a compression site provides an advantage over other conventional methodologies which do not allow for insertion of bone cement under relatively depressurized conditions. Manipulation of the injured site according to the methods described herein opens up the fracture to the structural height of a normal healthy vertebra. The void created by this manipulation allows insertion of the fracture treating material under depressurized conditions relative to the non-elevated compression fracture site. This is advantageous to the patient as the injured vertebra can be maintained at its pre-fracture/injury structural height after insertion and setting of the fracture treating material.

Also provided herein are methods and compositions for treating a compression fracture and other vertebral injuries, and in particular, methods and compositions are provided for treating an osteoporotic vertebral compression fracture. Compositions and methods herein are devoted to providing a fracture treating material into a compressed vertebra. In one embodiment, the fracture treating material is an expandable material having a similar or substantially similar modulus (modulus of elasticity or elastic modulus) as the cancellous bone of the injured vertebra. In some embodiments, compositions of the invention are provided based on the injured vertebra's location in the spine, e.g., cervical, thoracic, lumbar, as the different types of vertebra have different modulus values.

Elevation of Injured Vertebrae

Embodiments herein include elevation of an injured vertebral site, for example, a compressed vertebra site, prior to, and/or during administration of fracture treating materials. A compressed vertebra is any vertebra in a patient that has been compressed or squished to a height below that of a normal or healthy vertebra for that patient (see for example FIG. 1). Compression typically occurs in patients that have had a traumatic accident or that have osteoporosis, cancer or other like ailment. Although several of the embodiments herein are directed to compression fractures, it is envisioned that the subject matter is equally applicable to any damage to vertebrae requiring elevation or reduction of load on the injury site.

Elevation of an injury site alleviates pressure on the adjacent non-damaged vertebra by restoring normal anatomy as well as facilitates the amount and placement of material into the fracture site. Holding elevation of a site during placement of a fracture treating material is a significant improvement over state-of-the-art procedures which rely on the volume of the inserted material to elevate the site or use of wafers to incrementally elevate a site with rigid materials.

As described in more detail below, embodiments herein provide inserting one or more anchor points to allow leverage to be applied to the injured vertebra and elevate the injury prior to or during insertion of a fracture treating material. The anchor points are typically obtained through use of pins or screws, but can include any gripping mechanism such as a clamp which enables a physician to manipulate an injured vertebra. The anchor points can be placed at the injury site, above the injury site, below the injury site, to the side of an injury site, etc., typically determined by the surgeon to provide a most appropriate way of elevating the compressed vertebra. For example, it is contemplated that placement of the pins, in this regard, can be anywhere around the vertebra—anterior, posterior, lateral, through the pedicle, through the spinous process, in the vertebra above or below the injured vertebra, or anywhere else useful in manipulating the fracture site. The anchor points then are moved relative to each other or relative to the patient body to elevate the injury site of the vertebra. For example, posteriorly placed anchor points may be compressed toward each other at one or more pivot points thereby allowing for the elevation of an anterior compressed site in the vertebra in a wedging motion (see FIG. 5A). Various embodiments will be described herein, although any combination used to allow for this elevation and insertion of material is within the scope of the invention.

Although several of the embodiments herein are directed to the use of pins as anchor points, it is envisioned that the subject matter is equally applicable to gripping mechanism such as clamps which enable a surgeon to manipulate an injured vertebra.

In one illustrative embodiment, and as shown in one or more of FIGS. 1-11 (or various embodiments thereof), a pin or other like device is inserted by a surgeon or other health care professional into a right or left pedicle at the level of the compression fracture of a patient. The distal end of the pin is positioned through the pedicle and into or about the anterior third of the compression fracture. The opposite end of the pin extends out of the injured vertebra toward and out the posterior side of the patient. In one embodiment the inserted pin and vertebra form a substantially right angle. A second pedicle pin can be inserted and positioned into the pedicle not taken by the first pin, i.e., if the first pin was inserted in the right pedicle, the second pin would be inserted into the left pedicle (see FIG. 4). Pin insertion into bone can be performed as is well known in the art. The combined pins provide a leverage point on the left and right sides of the compression site ensuring that the elevation occurs in a consistent manner. Note that in some embodiments, the left and right pedicle pins are positioned in the pedicle within a sleeve (or right and left pedicle sleeve) to provide added capacity for applying leverage with the pedicle pins (see below).

In another aspect, the right and left pins are actually positioned laterally to the right and left pedicle, i.e., extrapedicular. In this embodiment, the extrapedicular pins have less bone to inhibit pin movement at the fracture site, which can, in some embodiments, be advantageous. This embodiment can be especially useful where the compression fracture is present in a thoracic vertebra.

As previously noted, hollow pins can be employed with an additional smaller diameter pin inserted through the pin to enhance the angle and capability of the pin to exert force on the vertebra. In effect, the smaller diameter pin is placed through the larger diameter, short sleeve pin which allows the smaller pin to pivot within the sleeve without having the bone restrict movement as the fracture is elevated. The smaller pin, in addition, can have enhanced ability to move within the fracture site. Hollow pins are contemplated herein as useful at any insertion site.

Figure 5A:
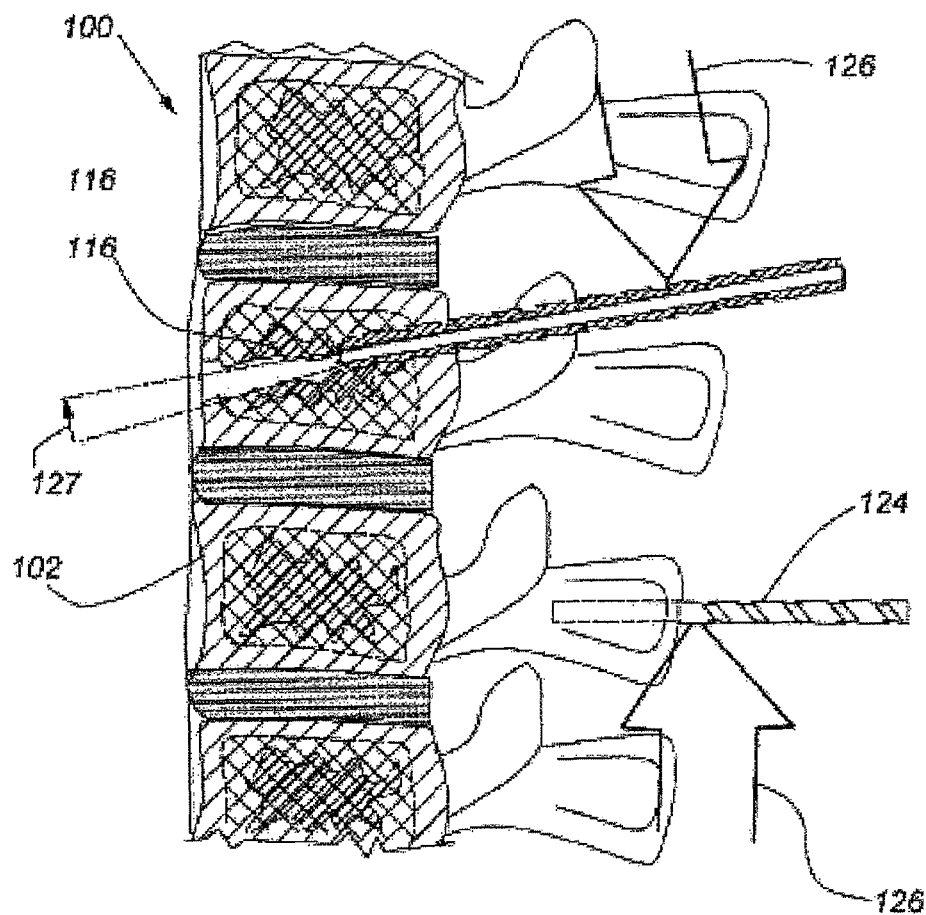
FIG. 5A is an illustration of the compressive force exerted on the pedicle and spinous pins in accordance with embodiments described herein.
Figure 5D:
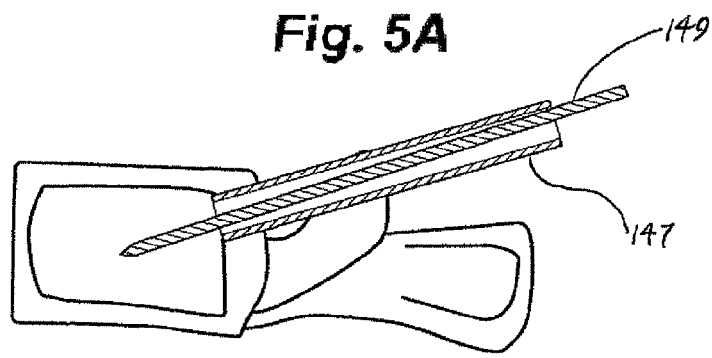
FIG. 5D shows a sleeve inserted into a pedicle and a pin inserted into the sleeve.
Figure 5B:
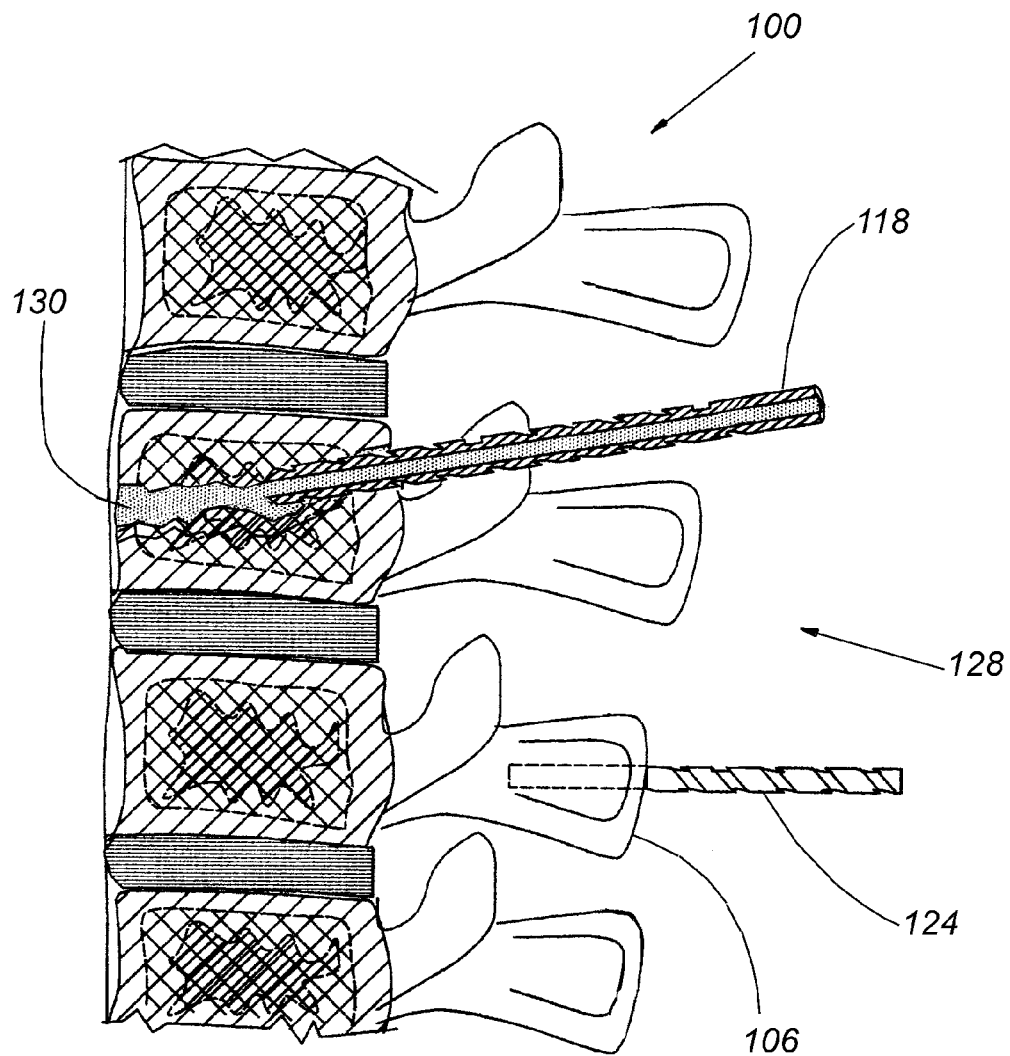
FIG. 5B shows the elevated injury site in accordance with embodiments described herein and FIG. 5C shows removal of the pedicle pin after insertion of the material into the injury site.

Illustratively as shown in FIG. 5D, a short hollow sleeve 147 with a large diameter would extend from the posterior cortex of the vertebral body to the posterior aspect of the pedicle. A pin 149 that would be used to elevate the fracture would go through the sleeve. The pin would have a much smaller diameter, for example, about 3 mm, or like a Steinman pin. The pin would have a pivot point on it, e.g. a ball, etc., which is the diameter of the sleeve. The pin can be inserted into the sleeve and to elevate the fracture. Without the sleeve, the pin movement can depend on the pedicle. Using the sleeve arrangement allows some independent movement of the pin relative to the pedicle. In some embodiments, this is important if the fracture cannot be elevated with the pin through the pedicle.

In yet another aspect, the at least two pins are positioned above the site of injury (through the pedicles or lateral to the pedicles). In this embodiment, the leverage point is above the fracture site, but pivot and leverage on the injured vertebra would be similar to the previously described embodiments. In any of these instances the anchor point is considered an upper anchor point.

Leverage is achieved by exerting force on the portion of the pin extending out from the vertebra. Leverage can be applied to one pin at a time, or to several pins relative to each other. For example, the pins can be compressed toward each other or can be moved away from each other, depending on how the surgeon determines the vertebra should be manipulated.

In some embodiments, one or more pins can be inserted into a spinous process of a vertebral segment below the fracture site. This pin is referred to herein as a spinous pin and is inserted to a depth that allows for secure placement of the pin and more particularly to a depth that allows for compressive force to be exerted on the placed pin (see below). The spinous pin extends from the posterior side of the patient's skin by at least 2 to 3 inches, although other variable lengths can be used based on the patients age, weight, musculature, bone density, etc (note also that length extensions can be used but may be considered more difficult to manipulate by the user). The spinous pin, in some embodiments, provides a lower anchor point. It is further contemplated that the lower anchor point can be provided in the same vertebra as the upper anchor point. In fact, any combination of pin locations are contemplated herein, including pins located in the same vertebra, different vertebra, pedicle, extrapedicular, spinous process, lateral corporeal, etc.

In other embodiments, only a single pin is used to elevate the fracture site. In such embodiments, a single pin is inserted into or just above or just below the fracture site. The patient's body weight could provide the necessary counter force on the other half of the vertebra as the surgeon manipulates the single pin to elevate the fracture site.

In another illustrative embodiment, a second set of two pedicle pins (or pins lateral to the pedicle) can be used to provide the surgeon or health care professional with the second leverage point at or below the fracture site. This second set of pins would be at a vertebral site below the site of injury and is again referred to herein as the lower anchor point.

As such, a variety of different pin positions can be used to establish the leverage or pressure points (upper and lower anchor points or lateral anchor points or a single anchor point) used to elevate the injured vertebra. Any number of these arrangements (pin position or number) is within the scope of the present invention as long as the arrangement provides elevation of the site through manipulation of the pins.

In some embodiments, each of the pins (pedicle, extrapedicular, spinous, etc.), or other like devices, have an engagement surface for enhanced capacity for the surgeon to grasp and manipulate. In addition, the pins can have engagement or binding surfaces to allow the two or more pins to be tied/bound together to hold the pins in position once the surgeon has elevated the fracture site.

Figure 6:
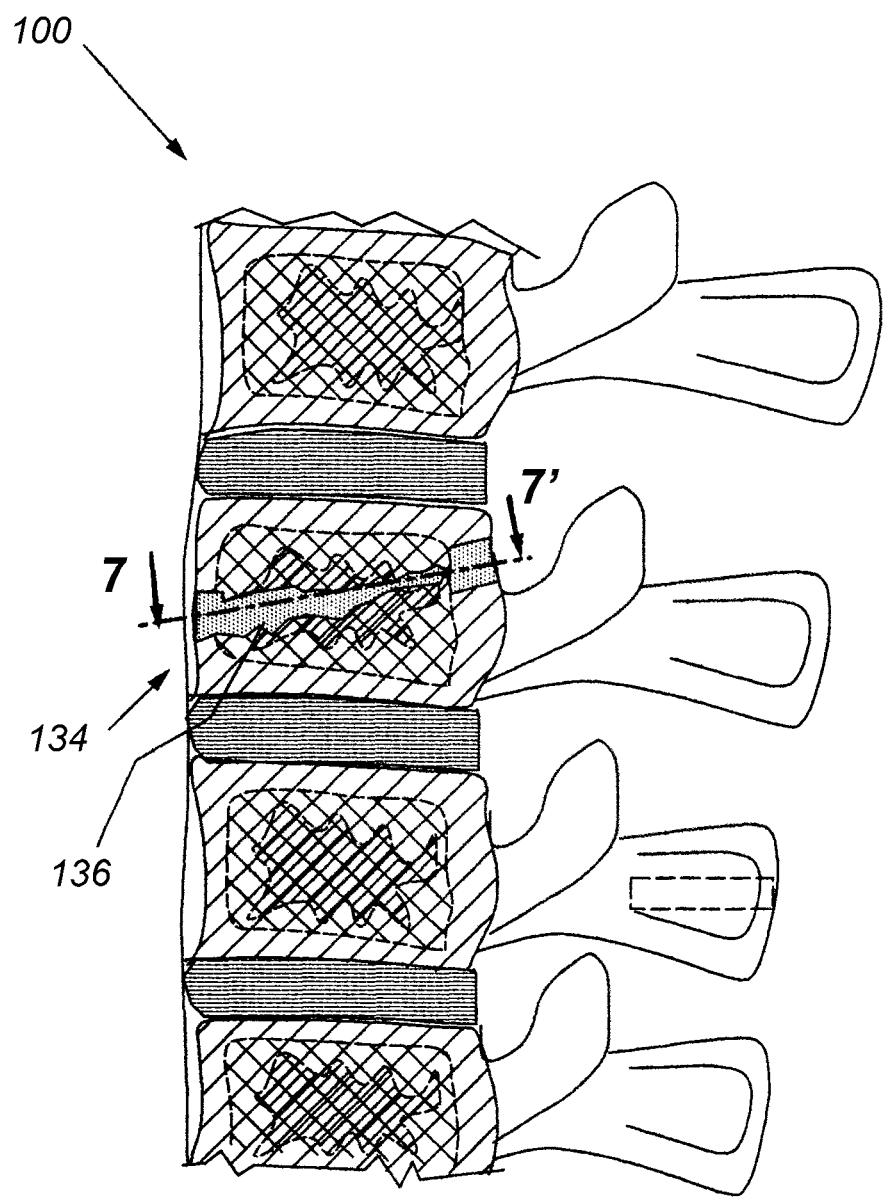
FIG. 6 is a cross-sectional view of a spine having been treated in accordance with embodiments described herein.

Illustratively, once emplaced in the patient, one or more pins at or above the point of injury can form one point of leverage (upper anchor point) and one or more pins below the point of injury can provide the other point of leverage (lower anchor point) for exerting force on the injured vertebra. Likewise, one or more pins on the left side of the vertebra can provide one point of leverage and one or more pins to the right of the injury can provide another point of leverage for exerting force on the vertebral fracture. In some embodiments, a compressive force exerted by the surgeon or other like health care provider forces two or more leverage points toward each other, for example, exerting compression on the posterior side of the injured vertebra and distraction on the anterior side. The action elevates the fracture as shown in FIG. 6. In other embodiments, the ends of the two or more pins are manipulated away from each other to elevate the fracture site.

As described above, any number of pins can be emplaced into the injury site as long as a surgeon is able to use the one or more pins to manipulate the pins to elevate the fracture site. Pin placement can be in the anterior, posterior, and/or lateral vertebra, can be above the injury site, below the injury site, or at the injury site. All sorts of leverage combinations are contemplated, including, for example, a single pin, two spinous process pins in the same spinous process, one spinous process pin in combination with one or more pedicle or extrapedicular pins, one or more anchoring sites below the injury site, one or more anchoring sites above the injury site, one or more anchoring sites lateral to the injury site, one or more anchoring sites at the injury site, one or more pedicle pins, one or more extrapedicular pins, and any combination thereof.

Elevation embodiments herein can be performed in combination with conventional fracture treating materials. In one embodiment, a method is provided to elevate a compression fracture site prior to, during, and/or after insertion of fracture treating material into the injured or compressed vertebra. As described herein, the phrase "fracture treating material"

includes conventional bone cements, modulus appropriate materials, and combinations thereof. It is understood by those skilled in the art that a modulus appropriate material is interchangeable with conventional bone cements, and as such, methods described herein are contemplated to employ both types of materials either separately or in combination.

A bone modulus appropriate material as described below has a modulus suitable for a particular patient, patient condition, bone type, etc. In some embodiments, the modulus appropriate material has a modulus similar to that of the vertebra in which an injury has occurred. Exemplary embodiments are described in combination with novel compositions described herein for repair of the compression fracture, however, methodologies described herein should not be limited to use of bone modulus appropriate materials. Rather it is envisioned that other state of the art bone cements can also be substituted for the bone modulus appropriate material, e.g., CORTOSS®, REFOBACIN®, Norian Skeletal Repair System Cements, OSTEOSPONGE® etc.

Anterior compression fractures are exemplary failure modes and are demonstrated throughout the figures, however, it is contemplated herein that other types of failure modes can be addressed using the methods and compositions of the present disclosure.

With reference to FIGS. 1-11, embodiments in accordance with the present invention are shown.

FIG. 1A shows a side perspective view of an uninjured spine 100 showing a vertebra 102 having a body 104, spinous process 106, traverse processes 108, and pedicles 110. A spinal cord 112 runs through the vertebra 102 and a disc 114 separates adjacent vertebrae. The spinous process, right and left traverse processes and right and left pedicles extend away from the posterior side of a patient.

FIGS. 1B and 1C illustrate a compression fracture of a vertebra in accordance with the present invention. The compression fracture 116 causes a loss in height to the body of the affected vertebra. FIG. 1C shows a anterior perspective view of the compression fracture 116, again illustrating the loss in height to the body of the vertebra.

FIG. 2 provides a cross-sectional view of an isolated vertebra incorporating an embodiment in accordance with the present invention. A compression fracture 116 in the body 104 of the vertebra 102 causes a depression of the vertebral height and a loss of vertebral body volume. A right and left pedicle pin 118 is inserted into and through the injured vertebra's pedicle 120, with the distal end 122 of each pin 118 being positioned in the fracture site. Note that the pedicle pin can be smooth or threaded depending on the mode of pin insertion. In addition, one or both pedicle pins 118 can be hollow and act as a conduit for insertion of the fracture treating material into the pre-elevated fracture site.

Figure 3:
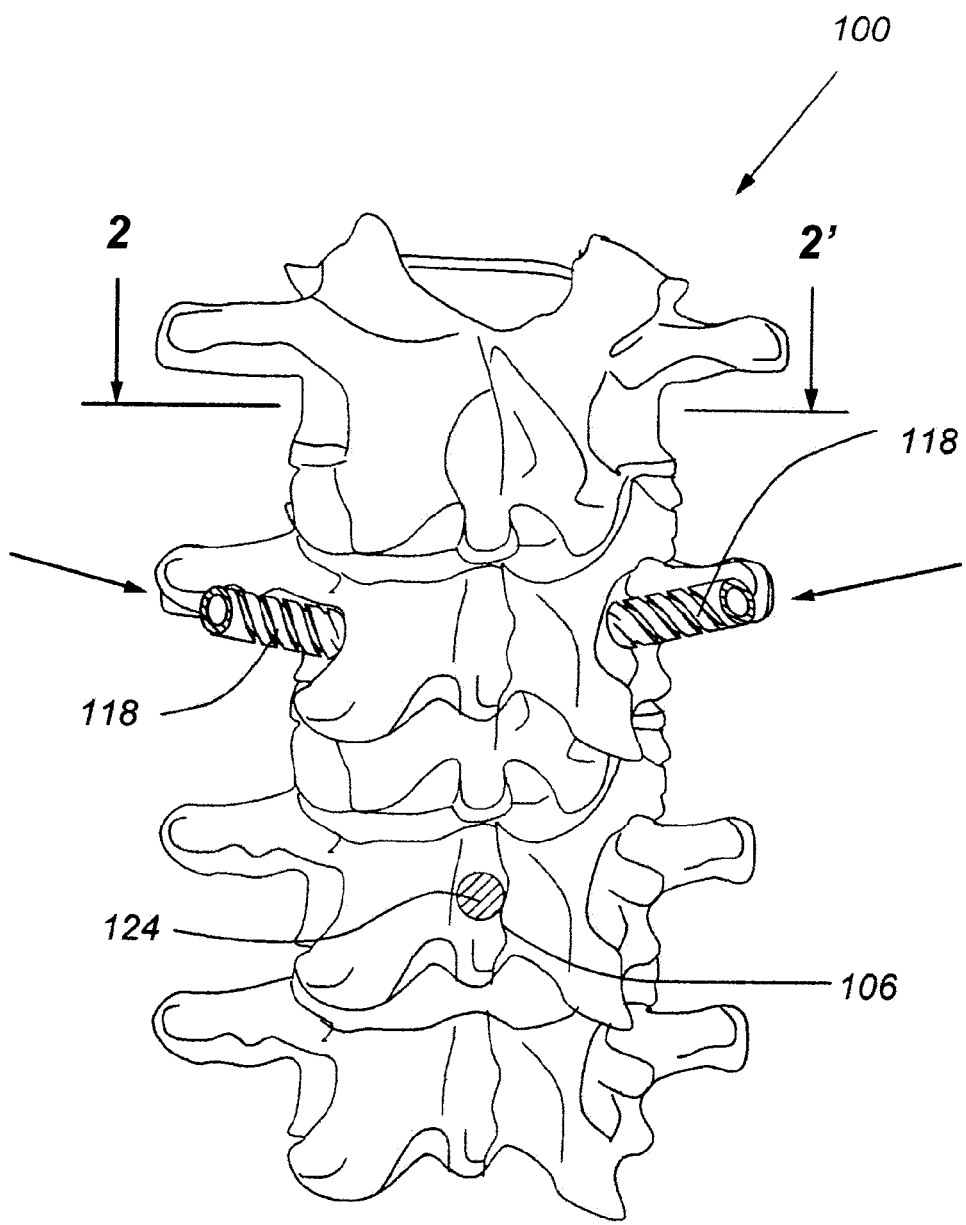
FIG. 3 is a posterior or oblique view of an injured vertebra in accordance with embodiments described herein.

With reference to FIG. 3, a spinous process pin 124 is shown extending from a spinous process 106 at a location below the site of injury. The pin 124 is anchored in the spinous process to provide a leverage point for compression between the pedicle pins and spinous process pin. Other pin arrangements are considered to be within the scope of the present disclosure as long as the two sets of pins provide force transmission points for elevation of the fracture.

Figure 4:
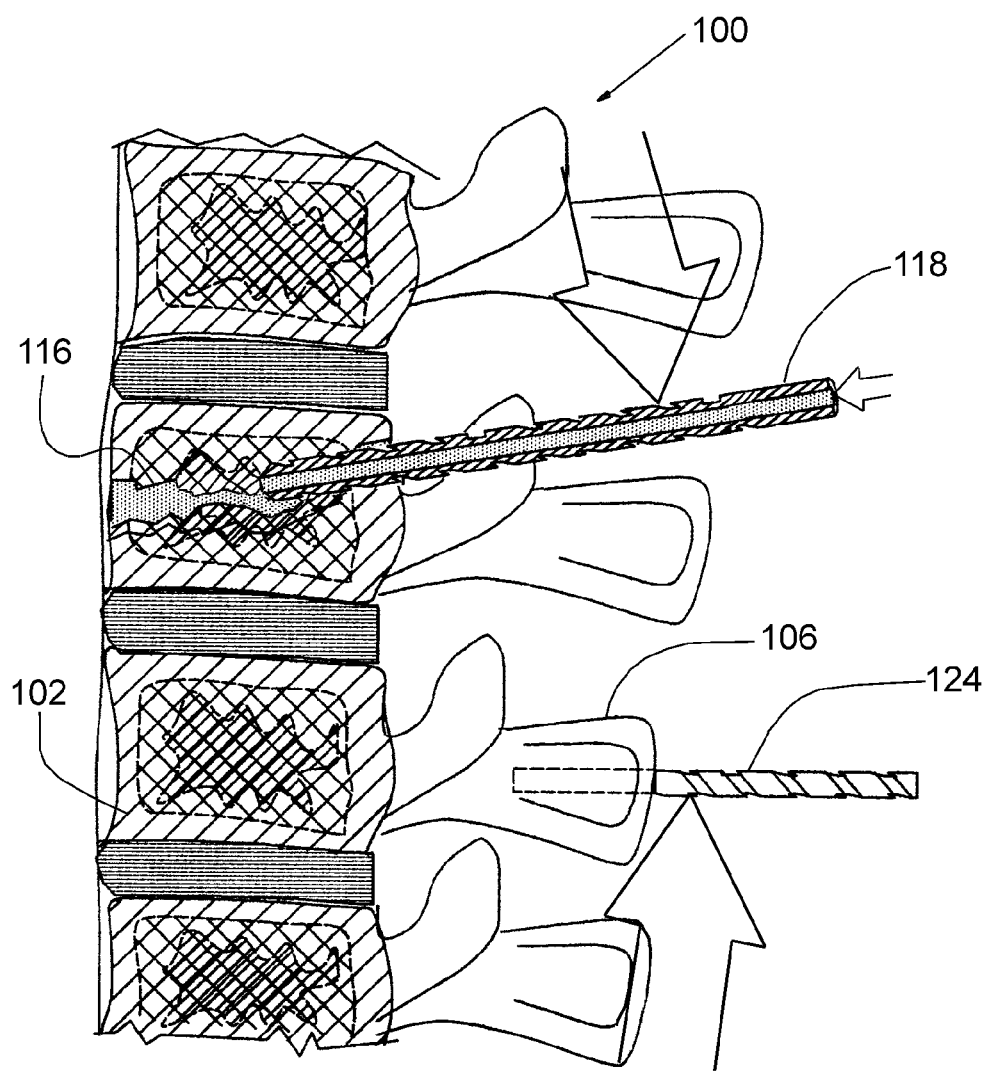
FIG. 4 is a cross-sectional view in accordance with line 4-4' of FIG. 2 in accordance with embodiments described herein.

FIG. 4 shows a cross-sectional view of a compression fracture 116 having embodiments in accordance with the present invention incorporated therein. A pedicle pin 118 extends through the vertebral pedicle and into the fracture providing a first leverage point. A spinous pin 124 is anchored in the spinous process 106 below the point of injury to provide a second leverage point.

Figure 5C:
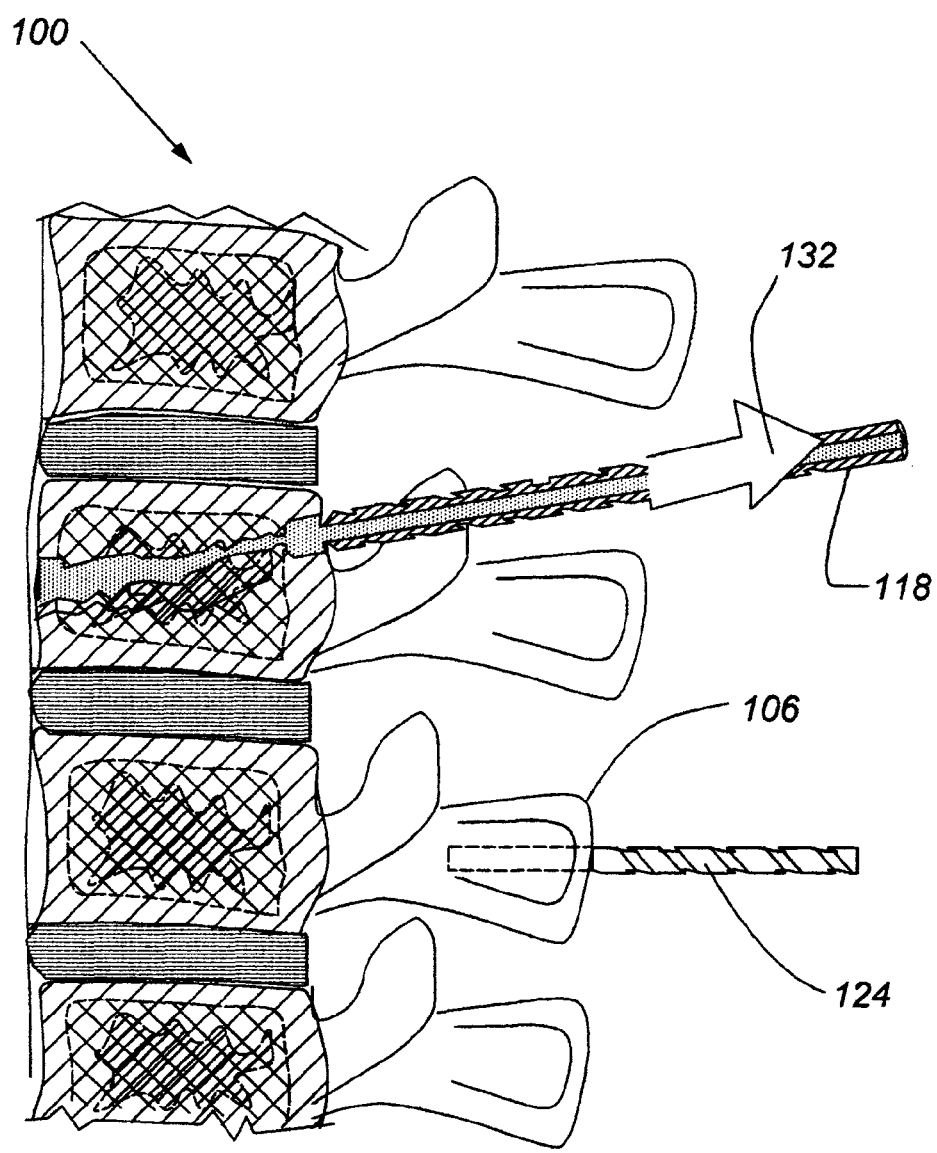
Figure 7:
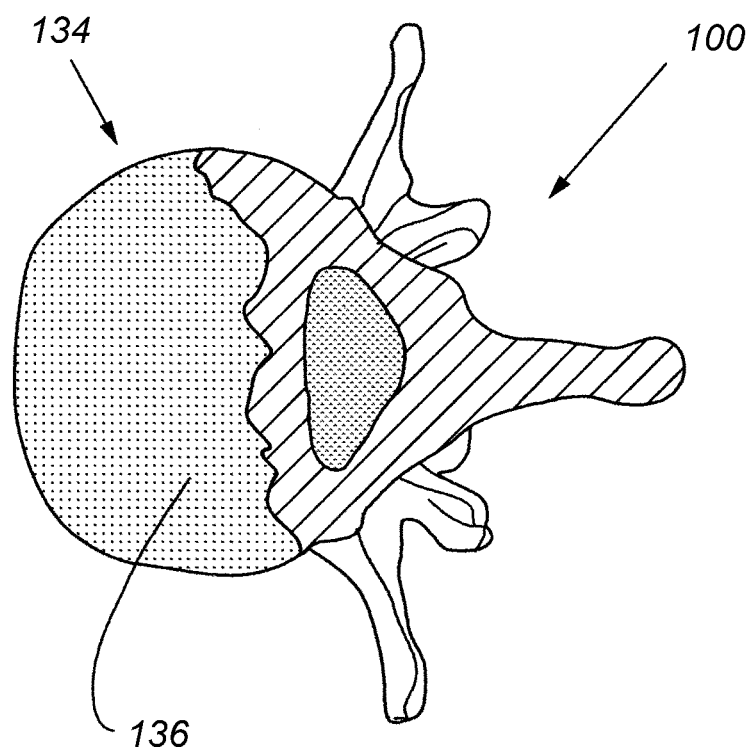
FIG. 7 is a horizontal cross-sectional view of a treated vertebra.

As shown in FIG. 5A, a compressive force (as illustrated by arrow 126) is exerted on the two leverage points to elevate the fracture site 116 and provide space for modulus appropriate material incorporation (see small arrow 127). The elevated fracture site is shown further in FIG. 5B. This elevated position 128 can be secured with any number of means by maintaining the compressive pressure on the two leverage points (not shown). In one embodiment, a modulus appropriate material is inserted through a pedicle pin and into the elevated fracture, as shown by the shaded area 130 in FIG. 5B. In some embodiments a piston is inserted and pushed through the hollow channel of the pedicle pin(s) to expel the modulus appropriate material into the fracture site and eliminate the potential for release of the material outside the injured vertebra (piston not shown). After an appropriate amount of time, the modulus appropriate material is set and the compressed leverage points can be released. As shown in FIG. 5C, the pedicle pin 118 is then removed (see arrow 132). Finally, as shown in FIGS. 6 and 7, a repaired vertebra 134 is shown from a lateral cross-sectional view and an oblique cross-sectional view taken along line 7-7' of FIG. 6. The repaired vertebra has an appropriate amount of modulus appropriate material incorporated therein and is less prone to re-injury than conventionally repaired vertebra (see shading 136). Note that the spinous pin would also be removed upon completion of the procedure.

Figure 8:
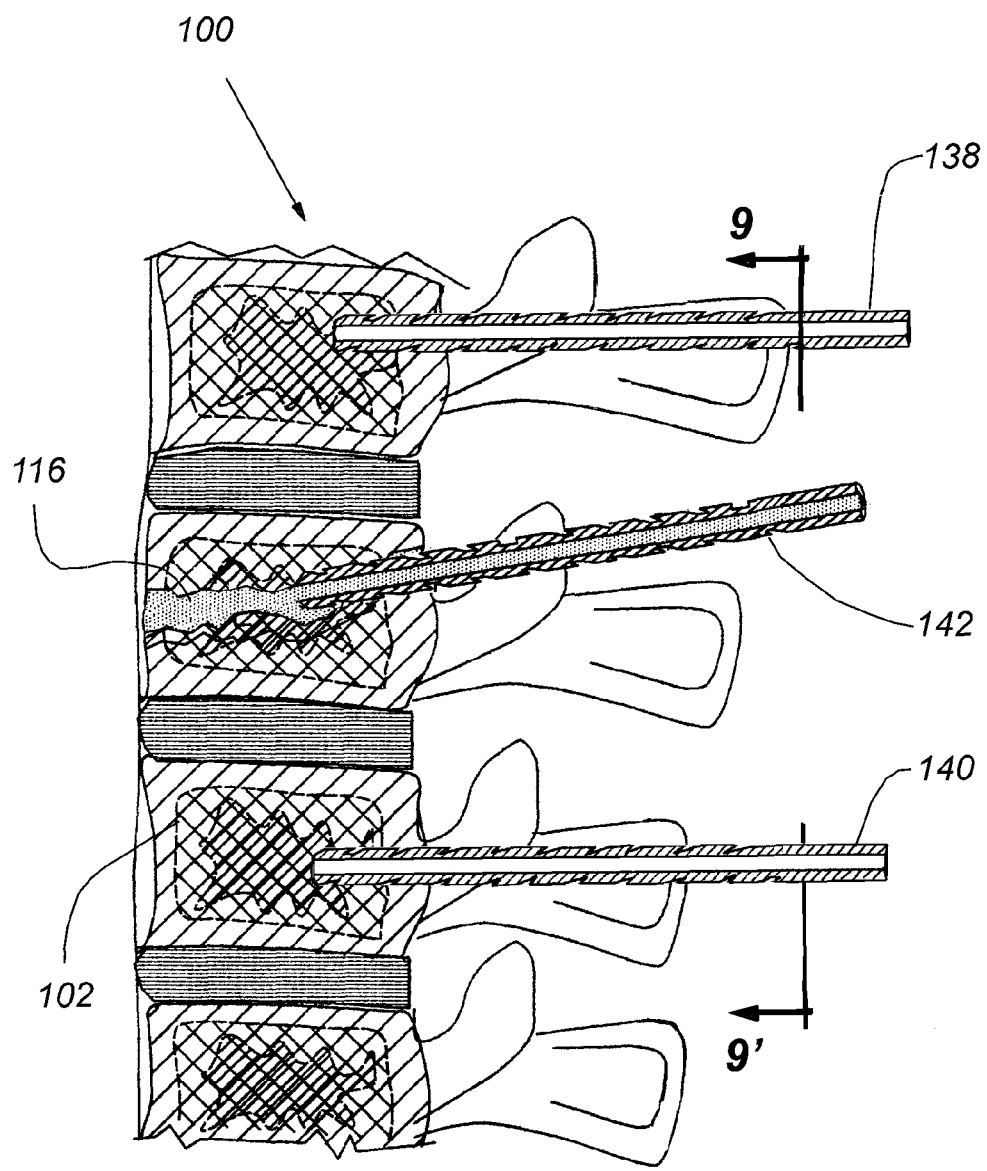
FIG. 8 is a cross-sectional view through an injured vertebra.
Figure 9:
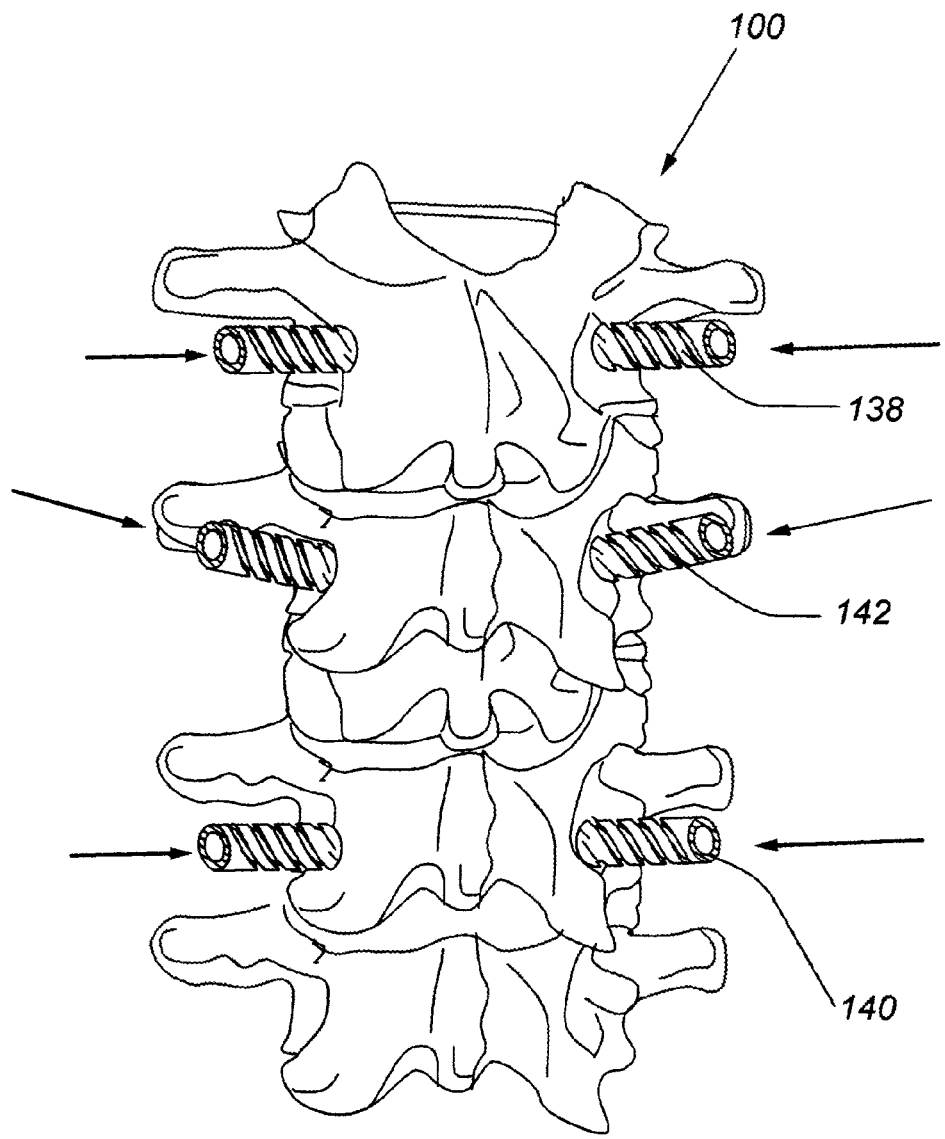
FIG. 9 is a perspective view of an injured vertebra in accordance with an embodiment described herein.

FIG. 8 shows an exemplary arrangement of leverage points for elevation of a fracture. In this embodiment, a pedicle-based or spinous process-based pin(s) is positioned above 138 and below 140 the fracture site 116. In this manner a pair of leverage points is obtained for exertion of compression and elevation of the fracture site. Forces are transmitted from the pins, to the vertebrae, through the discs adjacent the injured vertebrae, and to the end plates of the injured vertebra to elevate the fracture. Another instrument(s) 142 is inserted directly into the fracture site for delivery of the modulus appropriate material. This delivery device(s) 142 is not involved in fracture elevation, rather delivery of the material. FIG. 9 is a perspective view along line 9-9' of FIG. 8, again showing the two leverage points and a pair of delivery devices.

Figure 10:
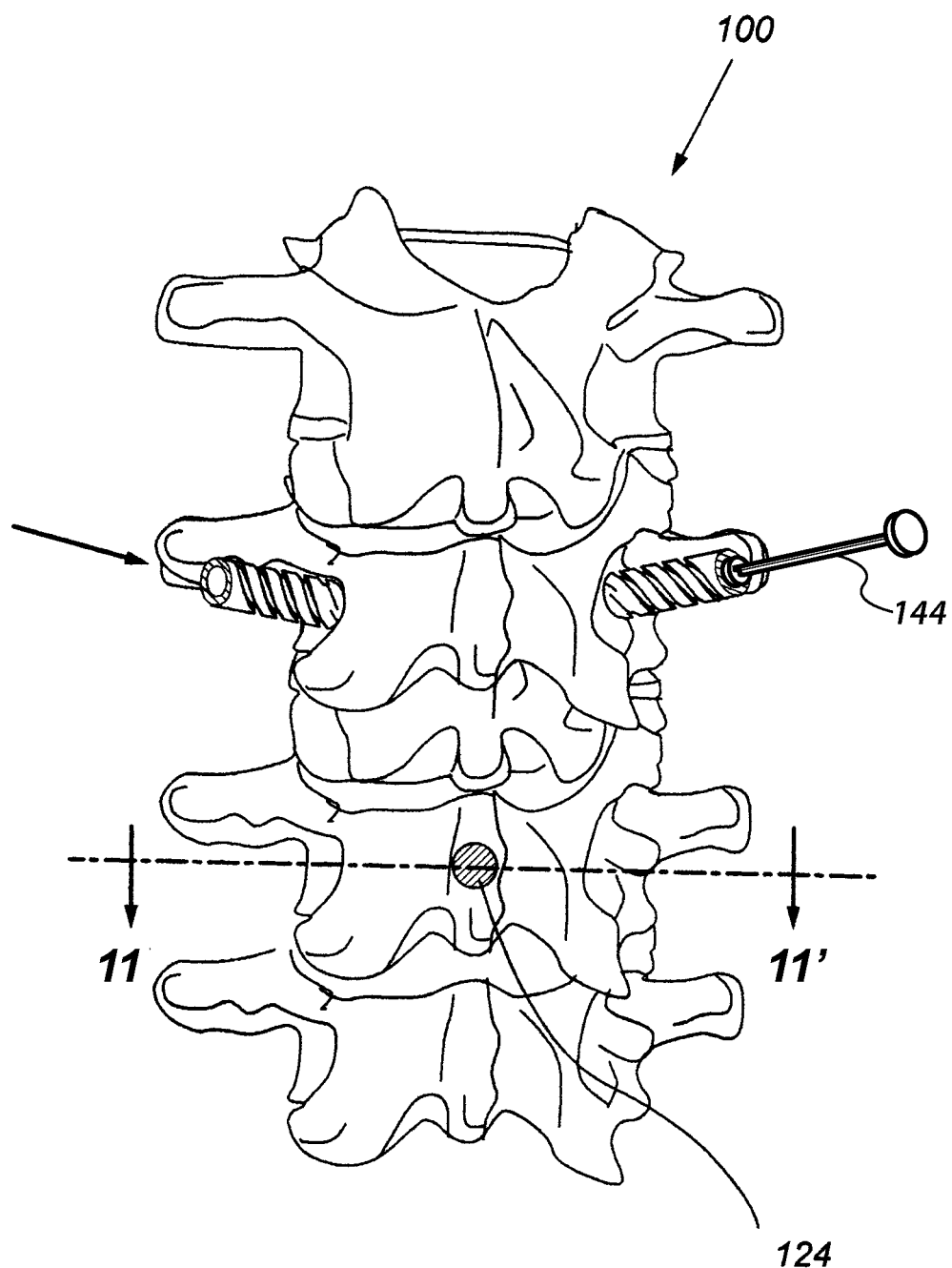
FIG. 10 is another perspective view of an injured vertebra showing hollow pedicle pins and a piston for delivery of the fracture treating material through the hollow pin.
Figure 11:
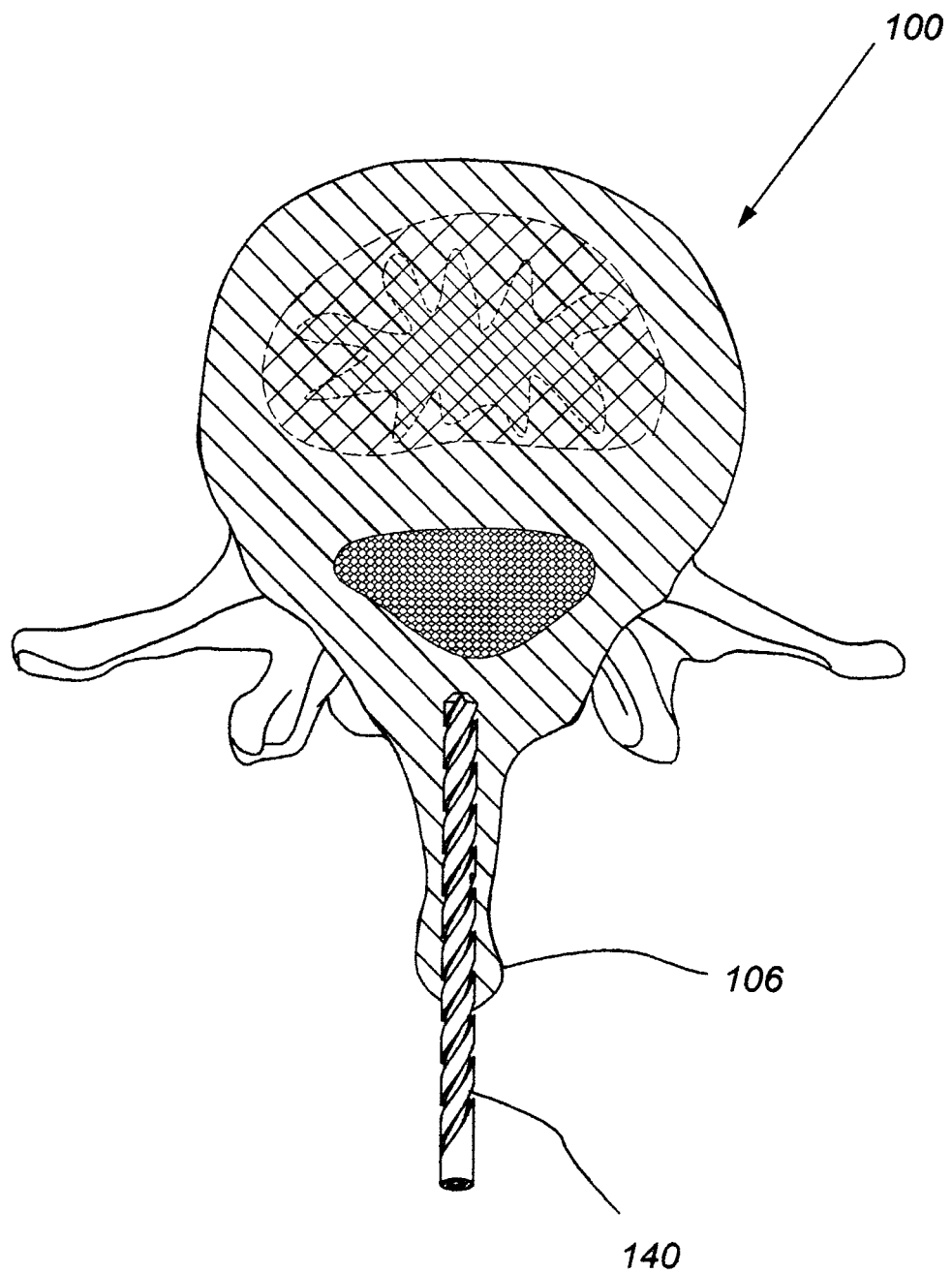
FIG. 11 is a cross-sectional view in accordance with line 11-11' of FIG. 10 in accordance with embodiments described herein.

FIGS. 10 and 11 provide a view where a pair of pedicle pins at the fracture site and a spinous process pin below the fracture site provide the leverage points used to elevate the fracture. In this embodiment, the pedicle pins are hollow and used as conduits for delivery of modulus appropriate material into the fracture. The left pedicle pin further shows a piston 144 within the hollow pin. FIG. 11 shows the positioning of the spinous process pin into the spinous process.

Compositions Having Similar or Substantially Similar Modulus as Damaged Vertebra Embodiments herein provide compositions for administration or injection into an injured or weakened vertebra. Compositions of the invention typically have a similar or substantially similar modulus to cancellous bone, and in some embodiments, a similar or substantially similar modulus of the particular vertebra (based on vertebra position within the spine) in need of repair.

A bone's modulus is a measure of that bone's stiffness. The modulus is defined as the ratio of stress over strain in a bone and is typically identified experimentally by determining a slope of a stress-strain curve created during testing known in the material's art (typically tensile or compressive testing). The mechanical properties of bone depend on the humidity, size of load on the bone, and the rate of loading and direction of the applied loading that a particular bone undergoes in the body.

Embodiments of the invention include the concept of identifying a modulus appropriate composition or material for use in treatment of a defect in a bone, and in particular, a compression fracture to a vertebra. As used herein, a "modulus appropriate composition or material" is one that is similar or substantially similar to the modulus of the bone or vertebra in need of treatment. A modulus appropriate composition or material can be a single composition or material or a combination of compositions and materials. As referred to herein, "treatment" is considered any improvement in the mechanical properties of a defective bone, for example, improvement in the stiffness of a fractured vertebra such that the treated vertebra is substantially immobilized.

In one embodiment, cancellous bone has a modulus of from 1 to 20 GPa and more typically a modulus of 3 to about 15 GPa. Modulus appropriate compositions and materials for use herein are injected into the injured or weakened vertebra, each composition having an ultimate modulus similar to the modulus for cancellous bone. In one embodiment, a composition is a hydrogel, an osmotic saline or an albumin solution. In some embodiments a mixture of these compositions can be utilized, for example, a composition having 50% hydrogel and 50% osmotic saline. Compositions of the invention can be modified to have the appropriate stiffness and mechanical properties to correspond to cancellous bone.

Embodiments of the present invention can also be focused on average modulus values for vertebrae in each of the cervical, lumbar, and/or thoracic spine. So, for a patient having an injured cervical vertebra, a modulus appropriate composition or material having a modulus in-line with cervical vertebra would be used as compared to a patient having an injured lumbar vertebra, where a composition with a modulus in-line with lumbar vertebra would then be used. In some cases, a patient with multiple compression fractures would have several different modulus appropriate compositions injected to different vertebra a first composition to a first vertebra and a second composition to a second vertebra (each appropriate to the vertebra within which it is used).

Average modulus values for cervical vertebrae are known within the art as are average modulus values for thoracic vertebrae and lumbar vertebrae. Note that modulus values can be modified for a specific patient's vertebrae based also on the patient's age, weight, presence of osteoporosis, and the like. For example, when an average modulus for a cervical vertebra is known, an older patient may have a cervical vertebra modulus of up to 30, 40 or 50% less (for example). These considerations can be reviewed in identifying the appropriate modulus appropriate composition of material for use in treatment of the patient's fracture. General description and enablement on bone modulus and mechanics of bone is provided in Bone Mechanics Handbook, $2^{nd}$ Ed., Stephen Cowin editor, 2001, Section III, which is incorporated herein by reference for all purposes.

The amount of composition injected into an injured vertebra is similar to levels used in "cement" based kyphoplasty. In general, enough material is injected into the vertebra to maintain the pre-compression structural parameters.

In alternative embodiments, compositions and materials of the invention include demineralized bone matrix (DBM), e.g., OSTEOSPONGE®, having a modulus similar to the modulus of the target injured vertebra. OSTEOSPONGE®, for example, is provided as variable sized single blocks or as filler in 0.5 cc, 1 cc, 2.5 cc, 5 cc, and 10 cc quantities—its malleable properties enable it to conform to and fill the void inside a hollow needle for application to a vertebra. DBM embodiments herein are inserted into the injured vertebra as a packed material and allowed to swell; the swelling maintains the compression fracture at a mechanical structure similar to that of an undamaged vertebra. Other DBM-like materials are contemplated as useful in the methods disclosed herein. Further, a resorbable tissue adhesive can be added to the DBM to immobilize the DBM in the fracture.

In each of these embodiments the modulus appropriate composition and/or material immobilizes and facilitates healing of the injured vertebra. The treated vertebrae fuse with a more consistent modulus throughout the bone and thereby avoid weak spots inherent with conventional therapies.

Methods for Treating an Osteoporotic Compression Fracture with a Modulus Appropriate Material Embodiments of the invention include methods for treating a patient having a vertebral compression fracture.

In one embodiment, a modulus appropriate material is identified for a particular patient. Identification can be based on an average modulus for cancellous bone, for example, using a modulus appropriate composition or material that conforms to the average modulus value for cancellous bone. Alternatively, embodiments include identification based on an average modulus for a patient's vertebral location, for example, using a modulus appropriate composition or material having an average modulus for cervical vertebrae. These determinations can be modified by the patient's age, weight, presence of osteoporosis or other like conditions, and the like. In another embodiment, testing can be performed on the patient to determine the specific modulus for the bone under need of repair, such modulus testing could be done as is known in the art.

Once the appropriate modulus appropriate material is selected, the patient is treated by administering the modulus appropriate material to the fractured vertebra, in accordance with the methods described herein. Administration of the material maintains the fracture at pre-injury structural parameters. In one embodiment, OSTEOSPONGE® is inserted into the fracture site before a modulus appropriate composition or material is added to the site to interdigitate with the OSTEOSPONGE®. The combination of materials holds and stabilizes the site, providing a permanent stabilization to the injured vertebra. For example, several small pieces of OSTEOSPONGE® would be pushed through the hollow pin or through the needle, one piece at a time, and then allowed to expand to fill the elevated fracture cavity. Once the fracture void is filled, a second composition, i.e., a modulus appropriate material, with glue-like properties can be added to the fracture site to prevent the OSTEOSPONGE® from migrating. Alternatively, a second composition of conventional bone cement, for example, KRYPTONITE™ Bone Cement or other settable adhesives or bone cements contemplated herein, is added to the OSTEOSPONGE® filled fracture cavity.

As needed, treated elevated fracture sites can also be treated with a resorbable tissue adhesive to help minimize motion and pain in the vertebra during vertebra healing.

In another embodiment, the fractured vertebra is elevated prior to or during the administration process of modulus appropriate materials (see above). In one aspect, the surgeon or other health care professional identifies the vertebral site of injury and prepares the patient for a procedure to that site. In this embodiment, the patient's posterior side is outward. The surgeon or other health care professional then inserts in any order the anchor points (gripping mechanism, pins, or otherwise) into the appropriate positions of the spine (as previously described). Where pedicle pins are used at the level of the injury, the pins can be hollow and can act as conduits for insertion of the modulus appropriate compositions into the injury site (and can include pedicle sleeves). All pins should be anchored sufficiently into the bone to allow manipulation of the injury site and elevation of the compression (and where required the anchor site strengthened using bone cement or other like material). Once secure, the surgeon or other health care professional exerts a force on the two anchor points to transform the vertebra from a compressed to a restored condition. The action elevates the endplate of the fractured vertebra to pre-compressed dimensions and provides space for insertion of the modulus appropriate compositions, or in some cases, other conventional bone cement(s).

In one embodiment, the surgeon or other health care professional then secures the pins to hold the vertebra in the restored condition prior to modulus appropriate material insertion (or other conventional bone cement). Securing the pins (or two anchor points) can be accomplished with bands, ties, plates, screws, wires, clamps or other like devices. Once the elevated injury site is secure, the composition is inserted into the fracture. Insertion of material can be via one or both of the pedicle pins or a separately inserted needle. Note that in some embodiments, the surgeon or other health care professional ensures that all the appropriate material has been inserted into the fracture site via a piston, i.e., the piston slides inside one or both pedicle pins to force the remaining material into the injury site (See, for example, FIG. 10).

Once the entirety of the material has been injected into the fracture site an appropriate amount of time is waited to ensure that the fracture site is set. This can range from one to twenty or so minutes and in some cases two to five minutes (time is dependent on amount injected and type of composition used for the particular patient's injury site among other things). After the fracture site has set with the injected material, the surgeon or other health care professional releases the securing device and allows the anchor points to be removed and thereby relieve the compressive force that elevated the injury site. In one embodiment, for example, pedicle pins and spinous pins are removed from the patient.

EXAMPLES

Example 1

An elderly female presents with pain, numbness, tingling, and weakness and a suspected vertebral compression fracture in conjunction with osteoporosis. After initial consultation and X-rays, CT scan, and/or MRI, the patient is admitted to the hospital for surgery.

In surgery, the physician identifies the vertebral site of injury and inserts two hollow pedicle pins, one each, into the right and left pedicles at the site of injury. A second set of pins is inserted below the injury. All pins are anchored to the bones to allow for manipulation of the injury site and elevation of the compression site. The upper pins are the upper levers, while the lower pins are the lower levers. The surgeon exerts a force on the upper levers and the lower levers to force the two sets toward each other. The effect is an elevation of the vertebra at the fracture site. The pins are fixed in the compressed state, and OSTEOSPONGE® is administered through the hollow upper pins into the injured site. The physician administers enough OSTEOSPONGE® to maintain the height of the compression site at pre-compression structural parameters. The OSTEOSPONGE® is allowed to set for 10 minutes, and then the physician removes the pins from the patient.

Example 2

A young male presents with extreme back pain and a vertebral compression fracture due to injury sustained from rock climbing accident. After initial consultation and X-rays, CT scan, and/or MRI, the patient is admitted to the hospital for surgery.

In surgery, the physician identifies the vertebral site of injury and inserts two hollow pedicle pins, one each, into the right and left pedicles at the site of injury. A third pin is inserted below the injury. The three pins are anchored to the bones to allow the physician to manipulate the injury site and elevate the compression site. The surgeon exerts a force on the three levers forcing the pins toward each other elevating the vertebra at the fracture site. The physician secures the pins in a compressed state, and administers REFOBACIN® through the hollow pins into the injured site. The physician administers enough REFOBACIN® to maintain the height of the compression site at pre-compression structural parameters. The REFOBACIN® is allowed to set for 7 minutes, and then the physician removes the pins from the patient.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method for treating a compression fracture in a vertebra of a vertebral column of a patient in need thereof, comprising:
    providing at least three anchor points on the patient's vertebral column to elevate the compression fracture,
    wherein two of the at least three anchor points are positioned on the same vertebra of the patient's vertebral column at a first vertebral level, and wherein a third anchor point is anchored into a posterior exterior surface of a spinous process at a second vertebral level different than the first vertebral level; and
    administering an amount of a fracture treating material into the elevated compression fracture.

2. The method of claim 1, wherein the at least three anchor points are provided on a posterior side of the patient's vertebral column.

3. The method of claim 1, wherein at least one of the at least three anchor points is at or above the compression fracture.

4. The method of claim 1, wherein at least one of the least three anchor points is at or below the compression fracture.

5. The method of claim 1, wherein the at least three anchor points are moved simultaneously together to elevate the compression fracture.

6. The method of claim 1, wherein the at least three anchor points are provided by pins selected from the group consisting of pedicle pins, extrapedicular pins, spinous process pins, and screws.

7. The method of claim 1, wherein one of the at least three anchor points is hollow and is located in the same vertebra as the compression fracture.

8. The method of claim 7, wherein the fracture treating material is administered into the elevated compression fracture through the hollow anchor point.

9. The method of claim 7, wherein two of the at least three anchor points are hollow and wherein two of the at least two anchor points are located in the same vertebra as the compression fracture.

10. The method of claim 1, wherein the fracture treating material is a modulus appropriate material.

11. The method of claim 10, wherein the modulus appropriate material is composed of, or partially composed of, a demineralized bone matrix (DBM).

12. The method of claim 11, further comprising a second modulus appropriate material to interdigitate with the DBM.

13. The method of claim 12, further comprising a permanent or resorbable tissue adhesive.

14. The method of claim 10, wherein the modulus appropriate material is selected from the group consisting of a hydrogel, an osmotic saline, and an albumin solution.

15. The method of claim 1, wherein two of the at least three anchor points are oriented in a generally vertical plane relative to the vertebra.

16. A method for treating a compression fracture in a vertebra of a vertebral column of a patient in need thereof, comprising:

providing at least three anchor points on the patient's vertebral column to elevate the compression fracture, wherein two of the at least three anchor points are positioned on the same vertebra of the patient's vertebral column;

a third anchor point disposed in a posterior exterior surface of a spinous process of a vertebra; and administering an amount of a fracture treating material into the elevated compression fracture.

17. The method of claim 16, wherein the at least three anchor points are moved simultaneously together to elevate the compression fracture.

18. The method of claim 16, wherein the at least three anchor points are provided by pins selected from the group consisting of pedicle pins, extrapedicular pins, spinous process pins, and screws.

19. The method of claim 16, wherein one of the at least three anchor points is hollow.

* * * * *

UNITED STATES PATENT AND TRADEMARK OFFICE
CERTIFICATE OF CORRECTION

| | |
|---|---|
| PATENT NO. | : 9,149,319 B2 |
| APPLICATION NO. | : 12/565648 |
| DATED | : October 6, 2015 |
| INVENTOR(S) | : Jeffrey John Thramann |

It is certified that error appears in the above-identified patent and that said Letters Patent is hereby corrected as shown below:

Title page, Item (73), in "Assignee", in column 1, line 1, delete "LLC," and insert --Inc.,--, therefor On title page 2, in column 1, Item (56) under "Other Publications", line 3, delete "Intraarticular" and insert --Intra articular--, therefor Signed and Sealed this
Fourteenth Day of June, 2016

Michelle K. Lee
*Director of the United States Patent and Trademark Office*